(12) United States Patent
Matsui et al.

(10) Patent No.: US 10,024,779 B2
(45) Date of Patent: Jul. 17, 2018

(54) SAMPLE MEASURING APPARATUS AND SAMPLE MEASURING METHOD

(71) Applicant: SYSMEX CORPORATION, Kobe-shi, Hyogo (JP)

(72) Inventors: Kunihiko Matsui, Higashimorokata-gun (JP); Akiko Tamura, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 0 days.

(21) Appl. No.: 15/592,316

(22) Filed: May 11, 2017

(65) Prior Publication Data

US 2017/0241890 A1 Aug. 24, 2017

Related U.S. Application Data

(63) Continuation of application No. PCT/JP2015/081533, filed on Nov. 10, 2015.

(30) Foreign Application Priority Data

Nov. 14, 2014 (JP) ................................ 2014-232242

(51) Int. Cl.

| G01N 33/48 | (2006.01) |
|---|---|
| G01N 15/14 | (2006.01) |
| G01N 33/49 | (2006.01) |
| G01N 33/493 | (2006.01) |

(52) U.S. Cl.
CPC ....... *G01N 15/1425* (2013.01); *G01N 33/493* (2013.01); *G01N 33/4915* (2013.01)

(58) Field of Classification Search
CPC ........... G01N 15/0266; G01N 15/0656; G01N 2015/0038; G01N 27/62; G01N 15/14; G01N 15/1425; G01N 21/64; G01N 33/4915; G01N 33/493
See application file for complete search history.

(56) References Cited

U.S. PATENT DOCUMENTS

| 6,489,600 B1 | 12/2002 | Taguchi | |
|---|---|---|---|
| 8,269,952 B2 * | 9/2012 | Ueno | ................. G01N 15/1459 356/39 |

(Continued)

FOREIGN PATENT DOCUMENTS

| JP | 2001-067706 A | 3/2001 |
|---|---|---|
| JP | 2009-053020 A | 3/2009 |

*Primary Examiner* — Michael P Stafira
(74) *Attorney, Agent, or Firm* — Metrolexis Law Group, PLLC

(57) ABSTRACT

A sample measuring apparatus of an embodiment includes: a laser diode that applies laser light to a measurement specimen prepared from a sample; a detection unit that acquires optical information from a particle in the measurement specimen to which the laser light is applied; a drive circuit that supplies a direct-current drive signal to the laser diode; and a high-frequency conversion circuit that generates a potential that switches between a high level and a low level in a predetermined cycle to guide the drive signal outputted from the drive circuit to a second signal path which is different from a first signal path connected to the laser diode in the predetermined cycle, thereby converting the drive signal to be supplied to the laser diode into a high-frequency signal.

20 Claims, 10 Drawing Sheets

(56) References Cited

U.S. PATENT DOCUMENTS

2011/0188039 A1\* 8/2011 Aoyama ................ G01N 21/53
356/338
2013/0147565 A1\* 6/2013 Aoyama ................ H03B 17/00
331/94.1

\* cited by examiner

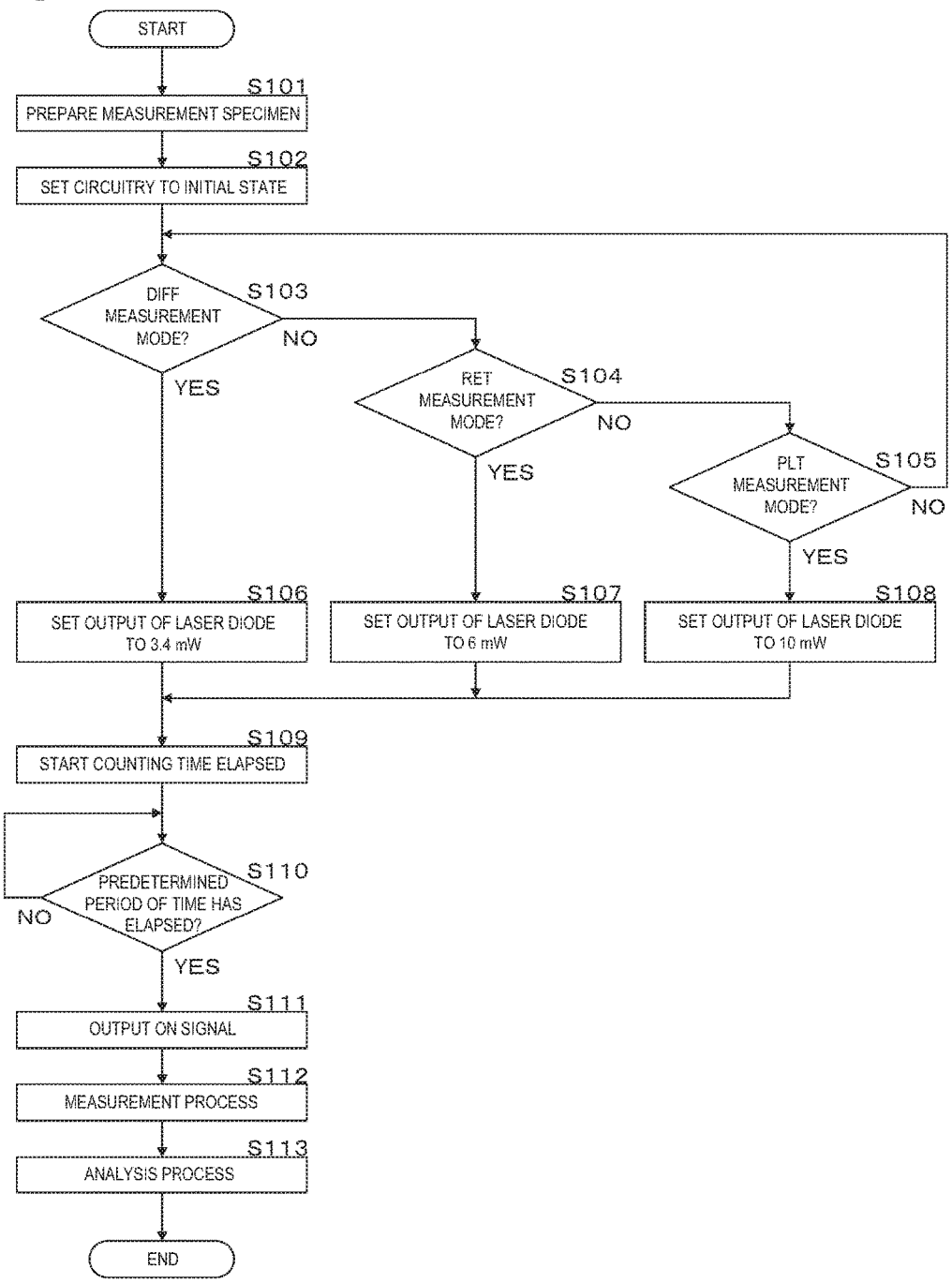

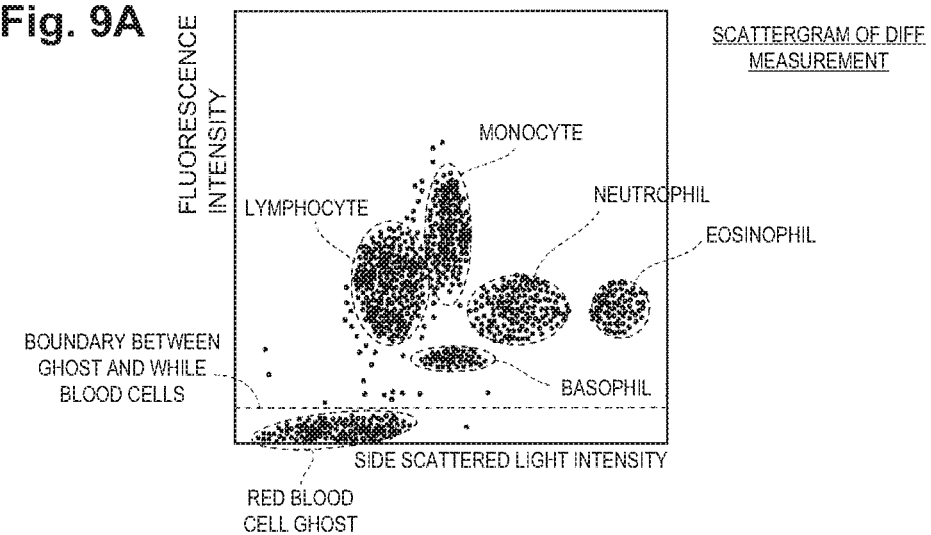
Fig. 9A  SCATTERGRAM OF DIFF MEASUREMENT
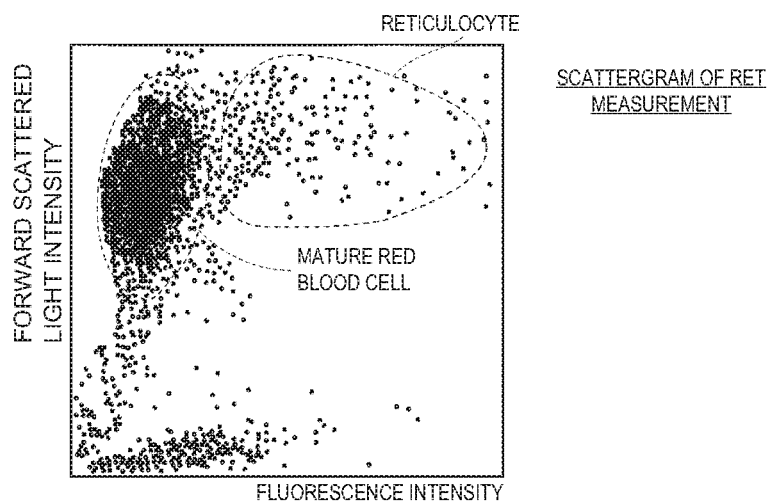
Fig. 9B  SCATTERGRAM OF RET MEASUREMENT
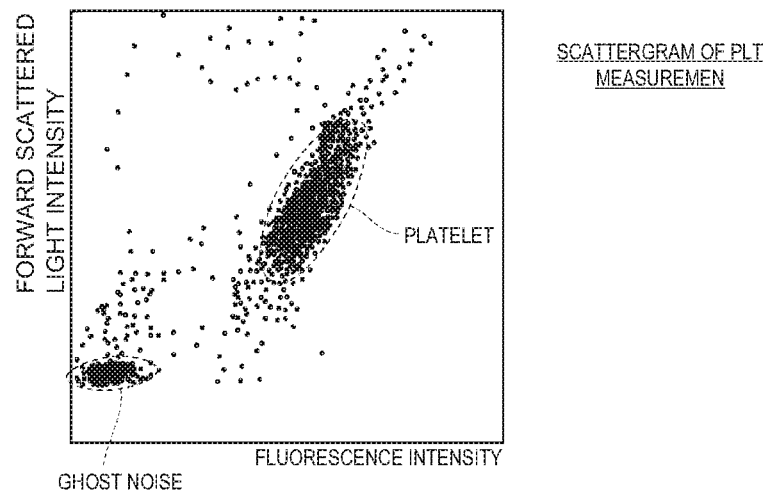
Fig. 9C  SCATTERGRAM OF PLT MEASUREMEN

SAMPLE MEASURING APPARATUS AND SAMPLE MEASURING METHOD

CROSS REFERENCE TO RELATED APPLICATIONS

This application is a continuation application of International Application No. PCT/JP2015/081533, filed on Nov. 10, 2015, entitled "SAMPLE MEASURING APPARATUS", which claims priority based on the Article 8 of Patent Cooperation Treaty from prior Japanese Patent Applications No. 2014-232242, filed on Nov. 14, 2014, the entire contents of which are incorporated herein by reference.

TECHNICAL FIELD

The disclosure relates to a sample measuring apparatus for measuring a sample.

BACKGROUND ART

A sample measuring apparatus has been known which measures a sample by applying laser light to a flow of a specimen prepared from the sample. The sample measuring apparatus uses a laser diode as a light source. The laser diode emits laser light of a single wavelength when continuously supplied with a drive current at a constant level. In such a single-mode oscillation state, factors such as a change in temperature of the laser diode cause a phenomenon in which the wavelength of the laser light changes stepwise. Such a phenomenon is called mode hopping.

In a specimen analyzer described in Japanese Patent Application Publication No. 2009-53020 (Patent Literature 1), a high-frequency component is superimposed onto a drive signal for a laser diode to set the laser diode to a multi-mode oscillation state. By adjusting the drive signal in this manner, the laser diode switches on and off in a short cycle, thereby suppressing the occurrence of mode hopping.

Laser diodes sometimes vary in output due to individual differences. In such a case, the specimen analyzer described in Patent Literature 1 uses an APC (Automatic Power Control) circuit to adjust the current of the drive signal for the laser diode such that the laser diode emits light with an expected output.

Also, sample measuring apparatuses sometimes switch the output of a laser diode in accordance with the measurement mode. The specimen analyzer described in Patent Literature 1 uses the APC circuit to adjust the current of the drive signal for the laser diode such that a different amount of light can be emitted for each of a DIFF measurement mode, an RET measurement mode, and a PLT measurement mode.

In the case of adjusting the current of the drive signal for the laser diode as above, the specimen analyzer described in Patent Literature 1 needs to perform complicated control via arithmetic processing by a microcomputer in order that the amplitude of the high-frequency signal to be superimposed onto the drive signal of the laser diode can be adapted to the drive signal for the laser diode.

SUMMARY

One or more embodiments of sample measuring apparatus may include: a laser diode that applies laser light to a measurement specimen prepared from a sample; a detection unit that acquires optical information from a particle in the measurement specimen to which the laser light is applied; a drive circuit that supplies a direct-current drive signal to the laser diode; and a high-frequency conversion circuit that generates a potential that switches between a high level and a low level in a predetermined cycle to guide the drive signal outputted from the drive circuit to a second signal path which is different from a first signal path connected to the laser diode in the predetermined cycle, thereby converting the drive signal to be supplied to the laser diode into a high-frequency signal.

One or more embodiments of sample measuring method may include: supplying a direct-current drive signal to a laser diode; generating a potential that switches between a high level and a low level in a predetermined cycle to guide, in the predetermined cycle, the drive signal to a second signal path which is different from a first signal path connected to the laser diode, thereby converting the drive signal to be supplied to the laser diode into a high-frequency signal; causing, based on the high-frequency signal, the laser diode to apply laser light to a measurement specimen prepared from a sample; and acquiring optical information from a particle in the measurement specimen to which the laser light is applied.

BRIEF DESCRIPTION OF DRAWINGS

FIG. 8 is a flowchart illustrating a process by a sample analyzer according to one or more embodiments.

FIGS. 9A to 9C are scattergrams illustrating results of a DIFF measurement, an RET measurement, and a PLT measurement according to one or more embodiments, respectively.

It is to be noted that the drawings are solely illustrative and do not limit the scope of the invention.

DESCRIPTION OF EMBODIMENTS

Description is given of embodiments of sample measuring apparatus constituting a part of a sample analyzer. The sample measuring apparatus is configured to acquire optical information necessary for analysis by applying laser light to a measurement specimen. The sample analyzer has a DIFF measurement mode for white-blood-cell measurement, an RET measurement mode for reticulocyte measurement, and a PLT measurement mode for platelet measurement. For each measurement mode, the sample measuring apparatus switches the output value of the laser light to be applied to the measurement specimen.

Embodiment 1

Figure 1:
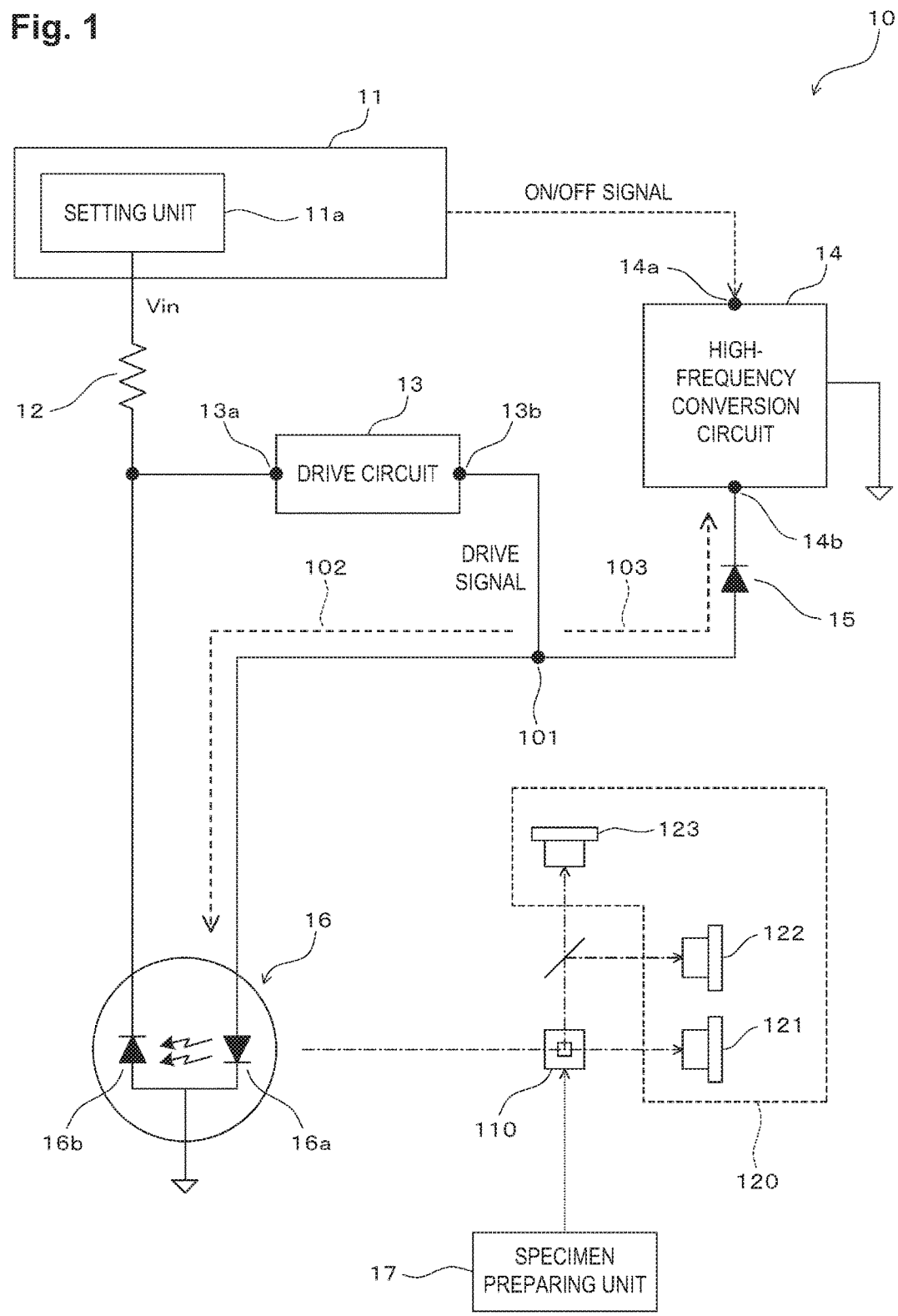
FIG. 1 is a diagram illustrating the configuration of a sample measuring apparatus according to one or more embodiments.

As illustrated in FIG. 1, sample measuring apparatus 10 includes controller 11, resistor 12, drive circuit 13, high-frequency conversion circuit 14, diode 15, laser light source 16, specimen preparing unit 17, flow cell 110, and detection unit 120. Controller 11 includes setting unit 11a that sets the output of laser light.

Laser light source 16 includes laser diode 16a and photodiode 16b. Laser diode 16a emits laser light by being driven by a drive signal supplied from drive circuit 13. Photodiode 16b receives laser light emitted from the back side of laser diode 16a and outputs a direct-current signal proportional to the intensity of the received light. This direct-current signal is hereinafter referred to as "monitor signal". Photodiode 16b serves to monitor the output of laser diode 16a. The monitoring of the output of laser diode 16a is not limited to such a back monitoring method, but may use a front monitoring method in which laser light emitted from the front side of laser diode 16a is partly divided and received.

Figure 2:
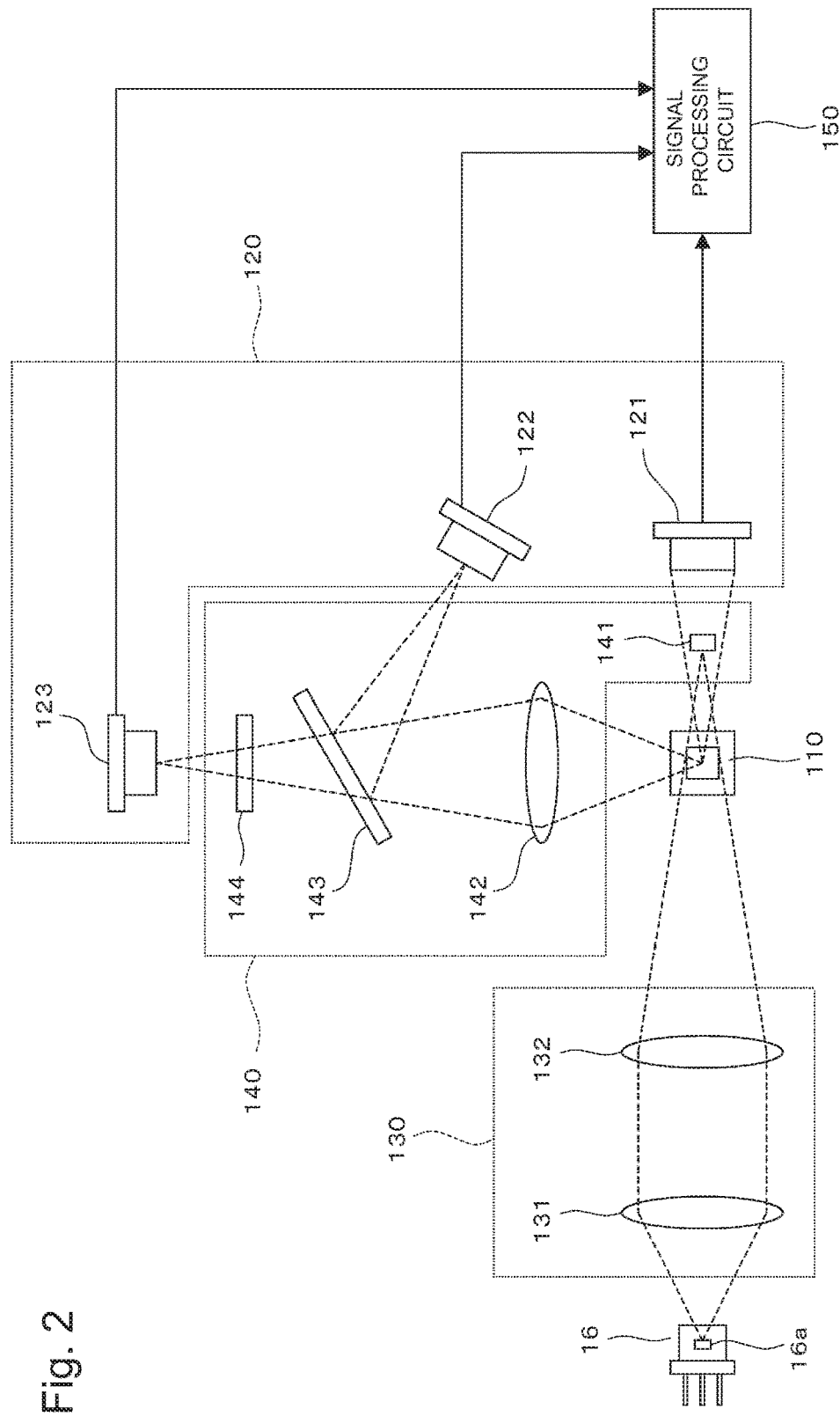
FIG. 2 is a diagram illustrating the configurations of a light-application optical system, a light-reception optical system, and a signal processing circuit according to one or more embodiments.

Detection unit 120 includes optical detectors 121 to 123. In addition to the configuration illustrated in FIG. 1, light-application optical system 130 and light-reception optical system 140 illustrated in FIG. 2 are disposed between laser diode 16a and detection unit 120. Optical detectors 121 to 123 receive forward scattered light, side scattered light, and fluorescence generated from a measurement specimen flowing through flow cell 110, respectively.

Setting unit 11a outputs voltage Vin such that the output of laser diode 16a can be a set value. Setting unit 11a switches voltage Vin in accordance with each of the measurement modes mentioned above. Voltage Vin from setting unit 11a is applied to resistor 12. When voltage Vin to be outputted from setting unit 11a is switched in accordance with the measurement mode, the current flowing into resistor 12 changes. Input part 13a of drive circuit 13 is connected to a signal line between resistor 12 and photodiode 16b.

Drive circuit 13 outputs a direct-current drive signal from output part 13b such that the current flowing through resistor 12 and the monitor signal generated at photodiode 16b come to equilibrium. Photodiode 16b and drive circuit 13 constitute an APC circuit that maintains the output of laser diode 16a at a value set by setting unit 11a.

Controller 11 outputs an ON signal or an OFF signal to input part 14a of high-frequency conversion circuit 14. The ON signal is a direct-current signal at a high level, and the OFF signal is a direct-current signal at a low level. High-frequency conversion circuit 14 is not in a high-frequency oscillation state during a period in which the OFF signal is inputted, and is set in the high-frequency oscillation state during a period in which the ON signal is inputted. Output part 14b of high-frequency conversion circuit 14 is connected through diode 15 to a signal line connecting output part 13b of drive circuit 13 and laser diode 16a.

In the high-frequency oscillation state, high-frequency conversion circuit 14 generates a pulse train signal pulsed in a predetermined cycle. High-frequency conversion circuit 14 outputs a pulse train signal with a potential switching between a high level and a low level in the predetermined cycle, from output part 14b. During periods in which the pulse train signal is at the low level, high-frequency conversion circuit 14 guides the drive signal outputted from drive circuit 13 to the ground from branching point 101 through second signal path 103 which is different from first signal path 102 connected to laser diode 16a, thereby converting the drive signal to be supplied to laser diode 16a into a high frequency signal. As a result, the drive signal outputted from drive circuit 13 is inputted into laser diode 16a in a pulse waveform pulsed at the predetermined cycle.

Diode 15 is connected between the signal line connecting the output part 13b of drive circuit 13 and laser diode 16a, and output part 14b of high-frequency conversion circuit 14. The cathode terminal of diode 15 is connected to output part 14b of high-frequency conversion circuit 14. In other words, diode 15 is disposed to cause current to flow only in the direction toward output part 14b of high-frequency conversion circuit 14. Thus, even when high-frequency conversion circuit 14 is set in the high-frequency oscillation state, a current based on the pulse train signal is not superimposed from output part 14b onto the drive signal for laser diode 16a.

As described above, the drive signal outputted from drive circuit 13 is guided at the predetermined intervals to the ground through output part 14b of high-frequency conversion circuit 14. Thus, laser diode 16a can be switched between an ON state and an OFF state in the predetermined cycle. Consequently, laser diode 16a is set to a multi-mode oscillation state. A specific circuit configuration of sample measuring apparatus 10 and the multi-mode oscillation of laser diode 16a are described later with reference to FIGS. 3 and 4, FIGS. 5A to 5D, and FIGS. 6A to 6D.

Specimen preparing unit 17 prepares a measurement specimen by mixing a sample and a reagent. The sample in embodiment 1 is blood collected from a test subject. Besides blood, the measurement-target sample for sample measuring apparatus 10 may be urine or epithelium. Even when the measurement-target sample is other than blood, sample measuring apparatus 10 also constitutes a part of a sample analyzer for analyzing the measurement-target sample.

Flow cell 110 lets the measurement specimen prepared by specimen preparing unit 17 flow through itself. Laser light emitted from laser diode 16a is applied to the measurement specimen flowing through flow cell 110. When the laser light is applied to the measurement specimen, light is generated from particles in the measurement specimen. Optical detectors 121 to 123 of detection unit 120 receive forward scattered light, side scattered light, and fluorescence generated from the particles in the measurement specimen, respectively, thereby acquiring optical information from the particles in the measurement specimen to which the laser light is applied.

As illustrated in FIG. 2, sample measuring apparatus 10 includes light-application optical system 130, light-reception optical system 140, and signal processing circuit 150.

Light-application optical system 130 includes collimator lens 131 and condenser lens 132. Collimator lens 131 converts the laser light emitted from laser diode 16a into parallel light. Condenser lens 132 condenses the laser light converted into the parallel light and applies it to flow cell 110. Thus, light-application optical system 130 applies the laser light emitted from laser diode 16a to the measurement specimen flowing through flow cell 110. When the laser light is applied to the measurement specimen, forward scattered light, side scattered light, and fluorescence are generated from particles in the measurement specimen.

Light-reception optical system 140 includes beam stopper 141, condenser lens 142, dichroic mirror 143, and spectral filter 144. Beam stopper 141 blocks rays of laser light transmitted by flow cell 110 without being applied to any particle among the rays of laser light applied to flow cell 110. Optical detector 121 is a photodiode. Optical detector 121 receives the forward scattered light and outputs an electric signal proportional to the intensity of the forward scattered light.

Condenser lens 142 condenses the side scattered light and the fluorescence. Dichroic mirror 143 reflects the side scattered light and transmits the fluorescence. Optical detector 122 is a photodiode. Optical detector 122 receives the side scattered light and outputs an electric signal proportional to the intensity of the side scattered light. Spectral filter 144 transmits the fluorescence. Optical detector 123 is an avalanche photodiode. Optical detector 123 receives the fluorescence and outputs an electric signal proportional to the intensity of the fluorescence. Thus, light-reception optical system 140 guides light generated from the measurement specimen to optical detectors 121 to 123 of detection unit 120. Optical detectors 121 to 123 may be photomultiplier tubes.

Signal processing circuit 150 performs predetermined signal processing on the electric signals outputted from optical detectors 121 to 123 to acquire measurement data on the forward scattered light, the side scattered light, and the fluorescence.

Next, the circuit configuration of sample measuring apparatus 10 is described with reference to FIGS. 3 and 4.

Figure 3:
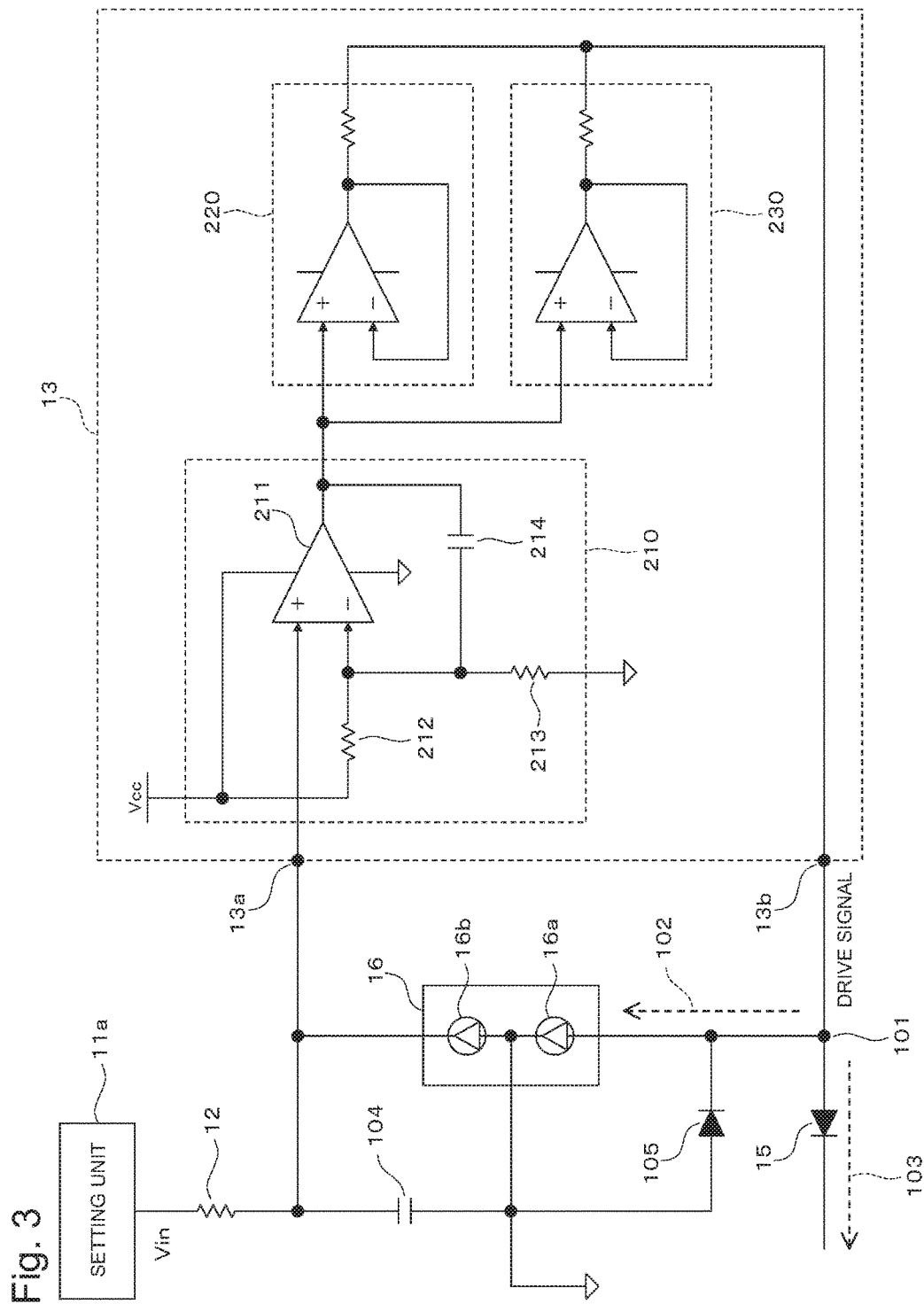
FIG. 3 is a diagram illustrating a circuit configuration of a sample measuring apparatus according to one or more embodiments.

As illustrated in FIG. 3, in addition to the circuit configuration in FIG. 1, sample measuring apparatus 10 includes capacitor 104 and diode 105. Capacitor 104 absorbs a noise component in the signal based on output voltage Vin from setting unit 11a to supply only the direct-current component to drive circuit 13. Diode 105 prevents application of reverse voltage to laser diode 16a to protect laser diode 16a.

Drive circuit 13 includes differential amplifier 210 and amplifiers 220 and 230. Differential amplifier 210 includes operational amplifier 211, resistors 212 and 213, and capacitor 214. Power-supply voltage Vcc is supplied to the voltage terminal of operational amplifier 211. Power-supply voltage Vcc is maintained at a constant voltage by a circuit including a filter and a capacitor. The ground terminal of operational amplifier 211 is connected to the ground.

The positive input terminal of operational amplifier 211 is connected to input part 13a of drive circuit 13. A reference voltage obtained by dividing power-supply voltage Vcc with resistors 212 and 213 is applied to the negative input terminal of operational amplifier 211. The reference voltage is set to a predetermined value slightly greater than 0 V, e.g. 0.1 volt. This prevents a signal from flowing into laser diode 16a even when an undesired voltage signal is applied to the positive input terminal of operational amplifier 211 while laser diode 16a is not actuated.

Amplifiers 220 and 230 are connected in parallel to the output terminal of operational amplifier 211. Amplifiers 220 and 230 amplify the current outputted from differential amplifier 210. The currents amplified by amplifiers 220 and 230 are superimposed onto each other and guided to output part 13b of drive circuit 13. Consequently, a drive signal is generated.

With drive circuit 13 configured as above, the output of laser diode 16a is set to a set value in accordance with output voltage Vin from setting unit 11a, as described below.

When setting unit 11a starts outputting voltage Vin, this voltage Vin is simply applied to the positive input terminal of operational amplifier 211. As a result, the output of operational amplifier 211 rises, and a drive signal is outputted from output part 13b of drive circuit 13. The outputted drive signal drives laser diode 16a. When laser diode 16a is thus driven, photodiode 16b receives laser light emitted from laser diode 16a. As a result, photodiode 16b outputs a monitor signal proportional to the output of laser diode 16a. The monitor signal flows through photodiode 16b in the upward direction in FIG. 3 in proportion to the amount of the laser light emitted from laser diode 16a.

The monitor signal flows in the direction opposite to the direction of the current flowing from setting unit 11a to resistor 12. Hence, the voltage applied to the positive input terminal of operational amplifier 211 through input part 13a decreases from voltage Vin outputted from setting unit 11a. Consequently, the output of operational amplifier 211 rises gently. Accordingly, the current value of the drive signal outputted from drive circuit 13 also rises gently. With the rise of the current value of the drive signal, the output of laser diode 16a rises as well. Hence, the monitor signal outputted from photodiode 16b rises as well.

As the monitor signal rises, the voltage applied to the positive input terminal of operational amplifier 211 decreases gradually. Eventually, the current flowing through resistor 12 and the monitor signal come to equilibrium, so that the voltage applied to the positive input terminal of operational amplifier 211 becomes equal to the reference voltage. Then, the output of operational amplifier 211 stops rising, and the output of operational amplifier 211 becomes constant. Consequently, the current value of the drive signal applied to laser diode 16a is maintained at a predetermined level and therefore maintained at the set value set by setting unit 11a.

When the output of laser diode 16a changes due to a change in temperature or the like, the monitor signal outputted from photodiode 16b changes. In response, the output of operational amplifier 211 changes, and the output of laser diode 16a is set back to the set value. Also, when voltage Vin is changed by switching the measurement mode, the output of operational amplifier 211 is adjusted for voltage Vin thus changed. Thus, the output of laser diode 16a is maintained at a set value for the switched measurement mode.

Figure 4:
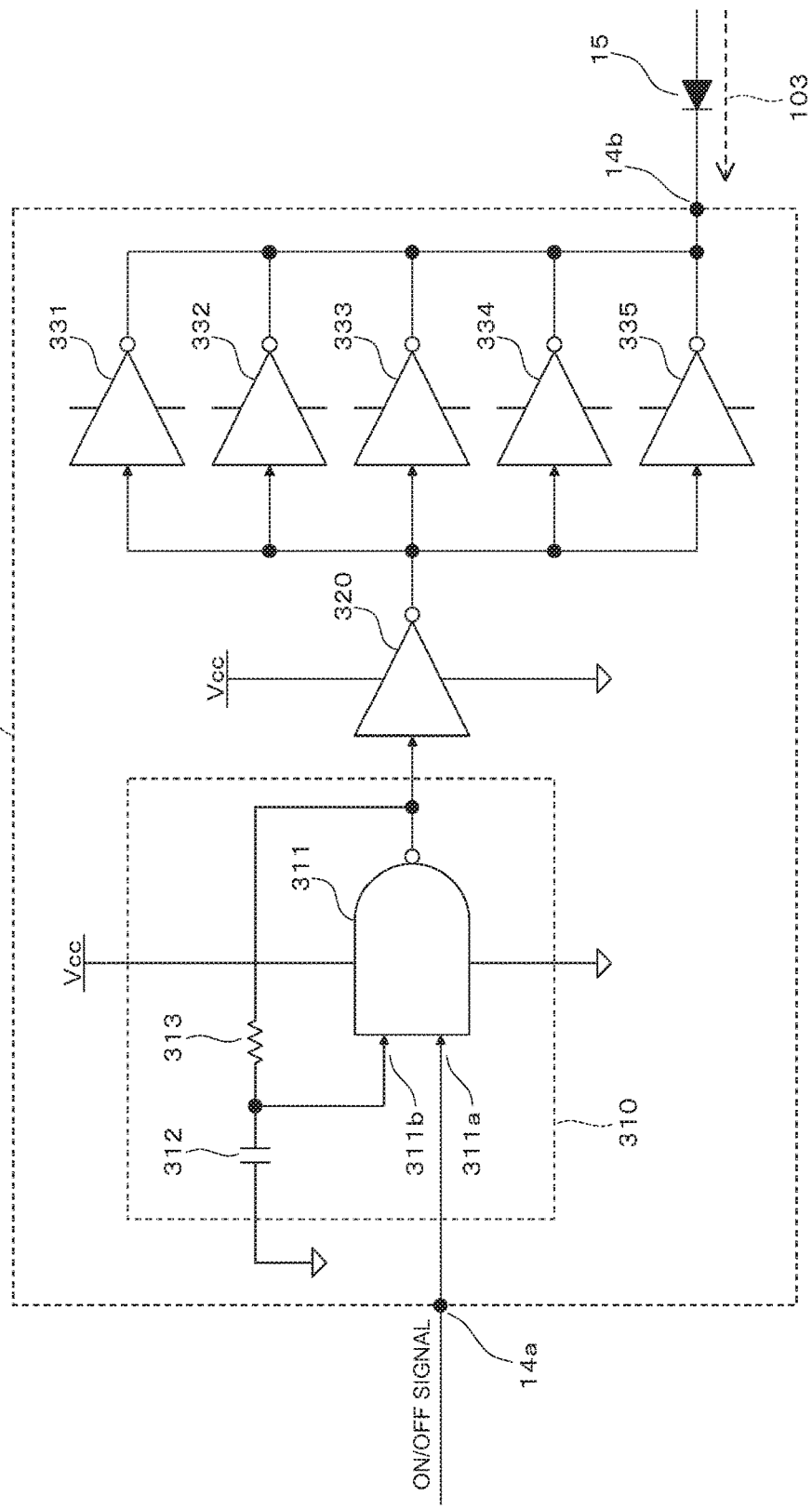
FIG. 4 is a diagram illustrating a circuit configuration of a sample measuring apparatus according to one or more embodiments.

As illustrated in FIG. 4, high-frequency conversion circuit 14 includes ring oscillator circuit 310, logic circuit 320, and logic circuits 331 to 335.

Ring oscillator circuit 310 includes logic circuit 311, capacitor 312, and resistor 313. Logic circuit 311 is a NAND circuit. Power-supply voltage Vcc is supplied to logic circuit 311. The ground terminal of logic circuit 311 is connected to the ground. One input terminal 311a of logic circuit 311 is connected to input part 14a of high-frequency conversion circuit 14. Controller 11 inputs an ON signal or an OFF signal into input terminal 311a. Other input terminal 311b of logic circuit 311 is connected to the ground through capacitor 312. The output terminal of logic circuit 311 is connected to input terminal 311b through resistor 313. Capacitor 312 and resistor 313 define the oscillation frequency of the signal to be outputted from logic circuit 311.

Logic circuit 320 is a NOT circuit. Power-supply voltage Vcc is supplied to the voltage terminal of logic circuit 320. The ground terminal of logic circuit 320 is connected to the ground.

Logic circuits 331 to 335 are NOT circuits. Logic circuits 331 to 335 are arranged in parallel to form multiple stages for the output terminal of logic circuit 320. Logic circuits 331 to 335 are housed in a single package. Power-supply voltage Vcc is supplied to the voltage terminals of logic circuits 331 to 335. The ground terminals of logic circuits 331 to 335 are connected to the ground through the package. The output terminals of logic circuits 331 to 335 are connected to output part 14b of high-frequency conversion circuit 14.

With high-frequency conversion circuit 14 configured as above, when controller 11 outputs an OFF signal to high-frequency conversion circuit 14, the potential at output part 14b of high-frequency conversion circuit 14 is fixed at a high level. Specifically, when the signal outputted from controller 11 to high-frequency conversion circuit 14 is an OFF signal, the signal inputted into input terminal 311a of logic circuit 311 is fixed at a low level. Hence, the output signal of logic circuit 311 is fixed at a high level. Then, the output signal of logic circuit 320 is fixed at a low level, and the output signals of logic circuits 331 to 335 are fixed at a high level. Consequently, the potential at output part 14b is fixed at a high level.

When controller 11 outputs an ON signal to high-frequency conversion circuit 14, the potential at output part 14b of high-frequency conversion circuit 14 is alternately switched between the high level and a low level. Specifically, when controller 11 outputs an ON signal to high-frequency conversion circuit 14, the signal inputted into input terminal 311a of logic circuit 311 is fixed at a high level. If the signal inputted into input terminal 311b of logic circuit 311 is at a low level, the output signal of logic circuit 311 shifts to the high level. When the output signal of logic circuit 311 shifts to the high level, the signal inputted into input terminal 311b shifts to a high level, so that the output signal of logic circuit 311 shifts to a low level. Thus, the output signal of logic circuit 311 is alternately switched between the high level and the low level.

Consequently, the output signal of logic circuit 320 and the output signals of logic circuits 331 to 335 are alternately switched between the high level and the low level as well. Hence, the potential at output part 14b is alternately switched between the high level and the low level. In other words, high-frequency conversion circuit 14 outputs a pulse train signal pulsed at the predetermined intervals.

Capacitor 312 and resistor 313 of ring oscillator circuit 310 define the frequency of the pulse train signal to be outputted by high-frequency conversion circuit 14. In embodiment 1, the frequency of the pulse train signal can be set to be high since capacitor 312 and resistor 313 can define the frequency of the pulse train signal. The frequency of the pulse train signal is set to be equal to or more than 85 MHz in order to maintain laser diode 16a in the multi-mode oscillation state. In embodiment 1, the frequency of the pulse train signal is set to be equal to or more than 85 MHz but not greater than 280 MHz. This frequency may just be a value that maintains laser diode 16a in the multi-mode oscillation state. Meanwhile, by including ring oscillator circuit 310, high-frequency conversion circuit 14 can be made simple and inexpensive.

During the periods in which the pulse train signal is at the high level, high-frequency conversion circuit 14 sets the value of the potential at output part 14b to a value greater than the potential at output part 13b of drive circuit 13. In this way, the drive signal outputted from drive circuit 13 does not flow into high-frequency conversion circuit 14 through output part 14b but flows into laser diode 16a during the periods in which the pulse train signal is at the high level. Also, even when the potential at output part 14b of high-frequency conversion circuit 14 is at the high level, diode 15 prevents current from flowing into laser diode 16a from high-frequency conversion circuit 14.

During the periods in which the pulse train signal is at the low level, high-frequency conversion circuit 14 sets the potential at output part 14b to 0. In this way, the drive signal outputted from drive circuit 13 does not flow into laser diode 16a but flows into high-frequency conversion circuit 14 through output part 14b during the periods in which the pulse train signal is at the low level.

Next, how laser diode 16a is set to the multi-mode oscillation state is described with reference to FIGS. 3 and 4, FIGS. 5A to 5D, and FIGS. 6A to 6C.

Figure 5A:
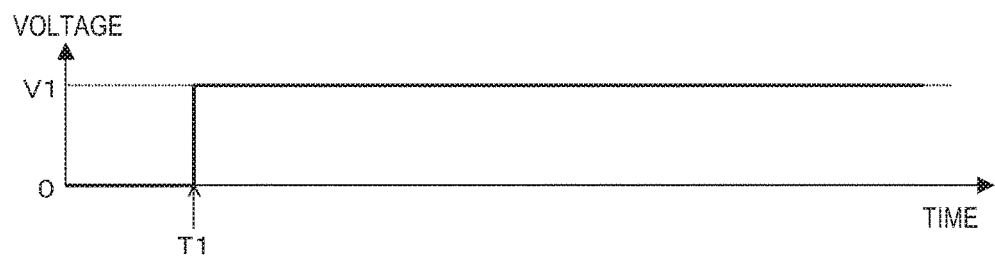
FIGS. 5A to 5D are time charts illustrating output voltage from a setting unit, an ON/OFF signal, a potential at an output part of a high-frequency conversion circuit, and a drive signal for a laser diode according to one or more embodiments, respectively.

Before a measurement operation starts, output voltage Vin from setting unit 11a is set to 0, and the signal outputted from controller 11 to high-frequency conversion circuit 14 is set to be an OFF signal. When the measurement operation starts, setting unit 11a outputs output voltage Vin of magnitude V1 at timing T1, as illustrated in FIG. 5A. In response, drive circuit 13 adjusts the current value of the drive signal such that the output of laser diode 16a becomes the set value. At this point, as illustrated in FIG. 5C, the potential at output part 14b of high-frequency conversion circuit 14 is maintained at the high level. The drive signal outputted from drive circuit 13 does not therefore flow into high-frequency conversion circuit 14. Also, with diode 15, current does not flow into laser diode 16a from high-frequency conversion circuit 14.

Figure 5B:
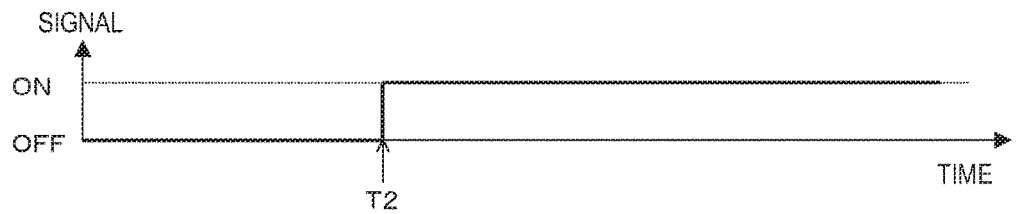
Figure 5C:
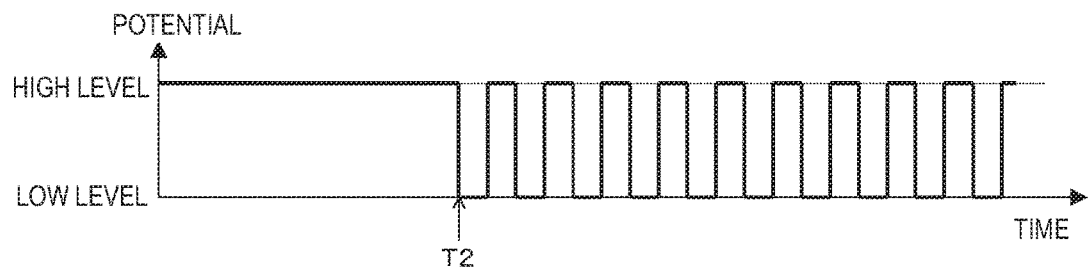
Figure 5D:
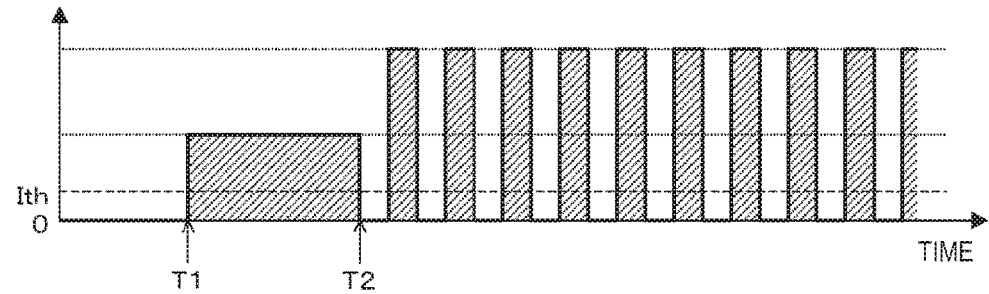

Thereafter, as illustrated in FIG. 5B, controller 11 outputs an ON signal to high-frequency conversion circuit 14 at timing T2. Timing T2 is set within a period in which laser diode 16a is in a transient response state. As illustrated in FIG. 5D, drive circuit 13 maintains the current value of the drive signal flowing into laser diode 16a at a predetermined level from timing T1 to timing T2.

As illustrated in FIG. 5C, once controller 11 outputs the ON signal to high-frequency conversion circuit 14 at timing T2, the potential at output part 14b of high-frequency conversion circuit 14 is alternately switched between the high level and the low level. In other words, high-frequency conversion circuit 14 outputs a pulse train signal pulsed in the predetermined cycle.

During the periods illustrated in FIG. 5C in which the pulse train signal is at the high level, the drive signal outputted from drive circuit 13 flows into laser diode 16a. During the periods illustrated in FIG. 5C in which the pulse train signal is at the low level, the potential at output part 14b of high-frequency conversion circuit 14 is 0 and is lower than the potential at output part 13b of drive circuit 13. Hence, the drive signal outputted from drive circuit 13 flows into logic circuits 331 to 335 through output part 14b of high-frequency conversion circuit 14 from diode 15 and is guided to the ground through the package from the ground terminals of logic circuits 331 to 335. Thus, the drive signal outputted from drive circuit 13 does not flow into laser diode 16a during the periods illustrated in FIG. 5C in which the pulse train signal is at the low level.

Thus, during the periods illustrated in FIG. 5C in which the pulse train signal is at the low level, the current value of the drive signal flowing into laser diode 16a is 0, which is less than threshold current Ith necessary for driving laser diode 16a, as illustrated in FIG. 5D.

When the current value of the drive signal flowing into laser diode 16a shifts to 0 as above, drive circuit 13 adjusts the current value of the drive signal such that the average output of laser diode 16a can be the set value. To this end, as illustrated in FIG. 5D, during the periods in which the pulse train signal is at the high level, the current value of the drive signal flowing into laser diode 16a is set to be twice greater than that during the period from timing T1 to timing T2. The current value of the drive signal flowing into laser diode 16a is greater than threshold current Ith during the periods in which the pulse train signal is at the high level.

In sample measuring apparatus 10 configured as above, the current value of the drive signal flowing into laser diode 16a is set to switch between a high level and a low level in the predetermined cycle, as illustrated in FIG. 5D. The frequency of the drive signal is the same as the pulse train signal from high-frequency conversion circuit 14 and is equal to or more than 85 MHz but not greater than 280 MHz. Since the drive signal has an amplitude with a high frequency as above, laser diode 16a can be set to a multi-mode oscillation state.

Figure 6A:
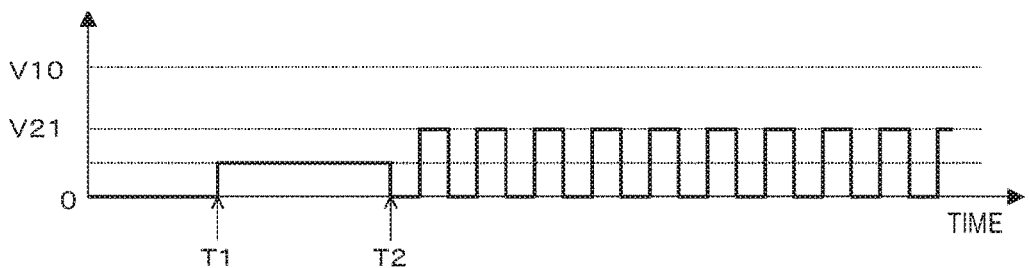
FIGS. 6A to 6D are time charts illustrating potentials at an output part of a drive circuit in a DIFF measurement mode, an RET measurement mode, and a PLT measurement mode and a potential at an output part of a high-frequency conversion circuit according to one or more embodiments, respectively.
Figure 6B:
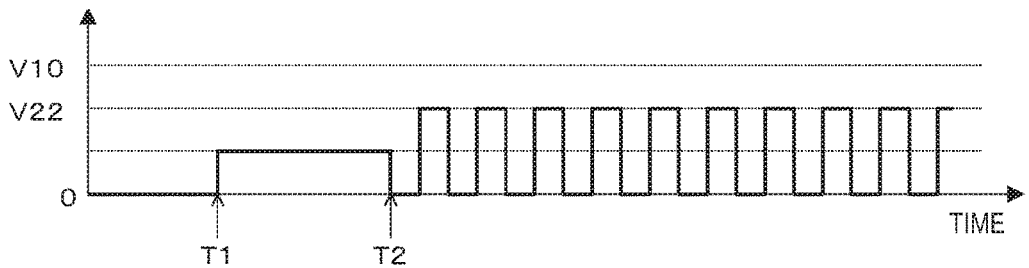
Figure 6C:
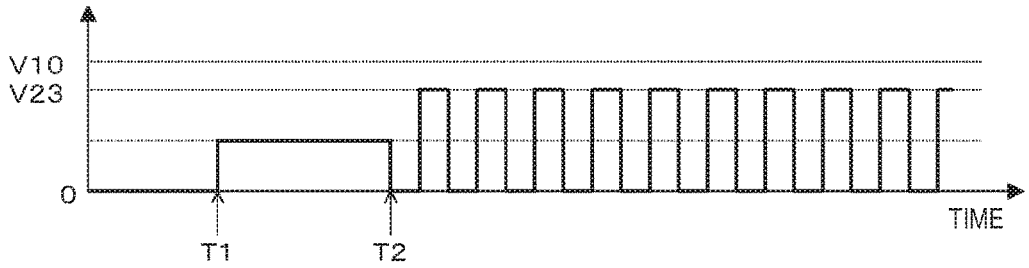
Figure 6D:
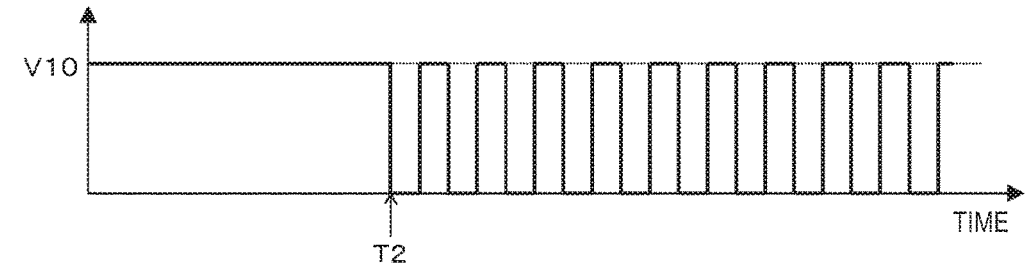

The potential of the pulse train signal during the periods in which the pulse train signal is at the high level is set to be higher than the potential at output part 13b of drive circuit 13 in any of the measurement modes mentioned above. Specifically, as illustrated in FIG. 6D, assuming V10 as the potential of the pulse train signal at the high level applied to output part 14b of high-frequency conversion circuit 14, potential V10 is greater than potential V21 at output part 13b in the DIFF measurement mode illustrated in FIG. 6A, greater than potential V22 at output part 13b in the RET measurement mode illustrated in FIG. 6B, and greater than potential V23 at output part 13b in the PLT measurement mode illustrated in FIG. 6C. Hence, in any of the measurement modes, it is possible to prevent the drive signal outputted from drive circuit 13 from flowing into high-frequency conversion circuit 14 and guide the drive signal to laser diode 16a during the periods in which the pulse train signal is at the high level.

Figure 7:
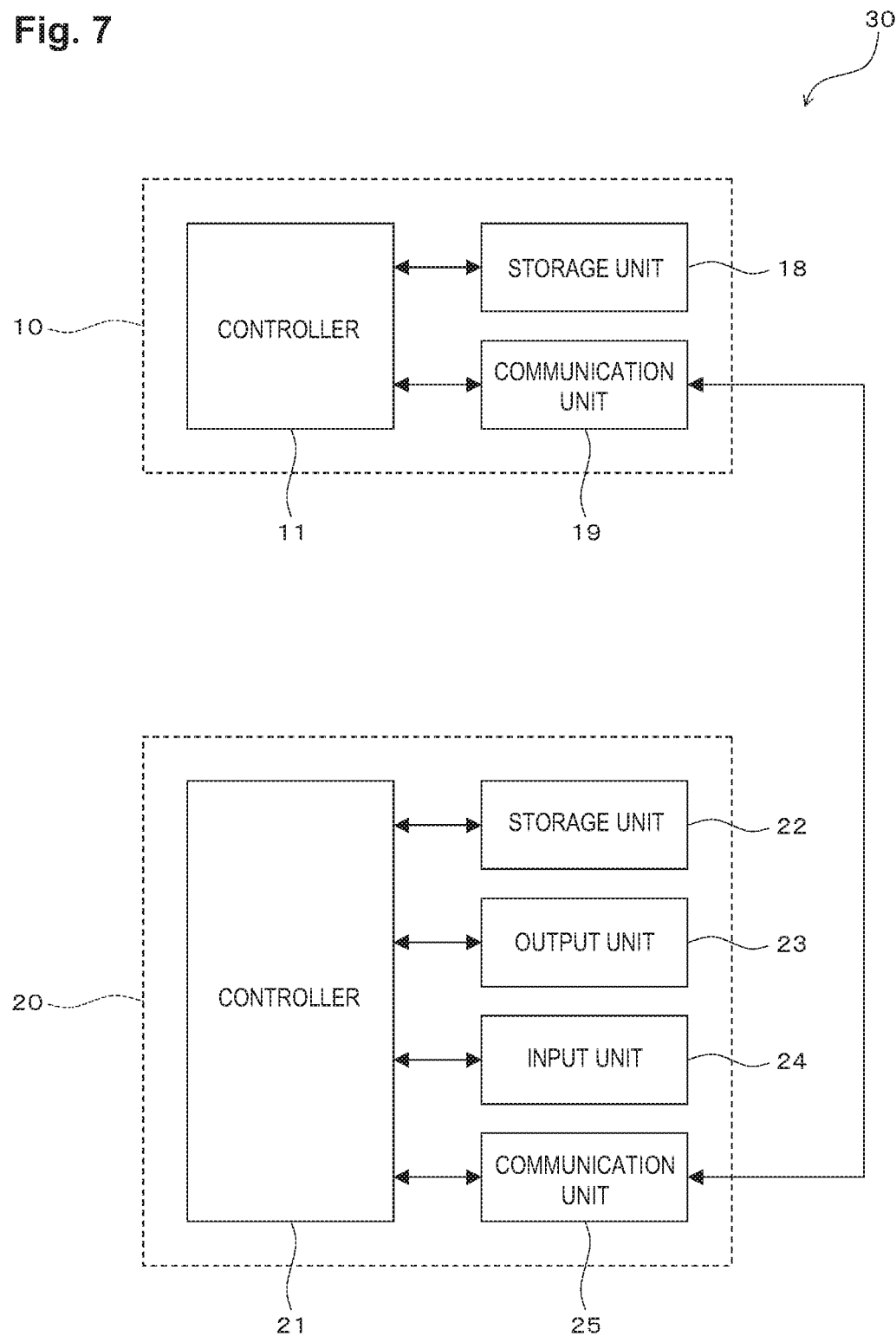
FIG. 7 is a block diagram illustrating the configuration of a sample analyzer according to one or more embodiments.

Next, sample analyzer 30 that analyzes a sample is described. As illustrated in FIG. 7, sample analyzer 30 includes sample measuring apparatus 10 and analyzer 20.

Sample measuring apparatus 10 includes the configurations illustrated in FIGS. 1 to 4, storage unit 18, and communication unit 19. Controller 11 receives signals outputted by components of sample measuring apparatus 10 and controls the components of sample measuring apparatus 10. Storage unit 18 stores measurement data obtained from measurements by sample measuring apparatus 10. Communication unit 19 communicates with communication unit 25 of analyzer 20.

Analyzer 20 includes controller 21, storage unit 22, output unit 23, input unit 24, and communication unit 25. Controller 21 receives signals outputted by the components of analyzer 20 and controls the components of analyzer 20. Storage unit 22 stores measurement data received from sample measuring apparatus 10 and analysis results obtained from analyses by analyzer 20. Output unit 23 is a display that displays textual information and graphical information. Input unit 24 receives inputs from the operator. For example, input unit 24 is a keyboard and a mouse. Communication unit 25 communicates with communication unit 19 of sample measuring apparatus 10.

Sample analyzer 30 may be made by integrating sample measuring apparatus 10 and analyzer 20. In this case, a single controller performs control for both measurement and analysis.

Next, a process by sample analyzer 30 is described with reference to FIG. 8.

Sample analyzer 30 can measure a sample in multiple measurement modes such as the DIFF measurement mode for measuring the white blood cells contained in the sample, the RET measurement mode for measuring the reticulocytes contained in the sample, and the PLT measurement mode for measuring the platelets contained in the sample. In step S101, specimen preparing unit 17 prepares a measurement specimen for the measurement mode. Specifically, specimen preparing unit 17 prepares a measurement specimen for white-blood-cell measurement in the case of the DIFF measurement mode, prepares a measurement specimen for reticulocyte measurement in the case of the RET measurement mode, and prepares a measurement specimen for platelet measurement in the case of the PLT measurement mode.

In step S102, controller 11 sets the circuitry to an initial state. Specifically, controller 11 sets output voltage Vin from setting unit 11a to 0 and sets the signal outputted to high-frequency conversion circuit 14 to an OFF signal.

In steps S103 to S105, controller 11 determines which one of the DIFF measurement mode, the RET measurement mode, and the PLT measurement mode the measurement mode is. If YES in step S103, that is, if the measurement mode is the DIFF measurement mode, step S106 is executed. In step S106, setting unit 11a sets output voltage Vin to a value for the DIFF measurement mode. As a result, the output of laser diode 16a is set to, for example, 3.4 mW.

If NO in step S103 and YES in step S104, that is, if the measurement mode is the RET measurement mode, step S107 is executed. In step S107, setting unit 11a sets output voltage Vin to a value for the RET measurement mode. As a result, the output of laser diode 16a is set to, for example, 6 mW.

If NO in steps S103 and S104 and YES in step S105, that is, if the measurement mode is the PLT measurement mode, step S108 is executed. In step S108, setting unit 11a sets output voltage Vin to a value for the PLT measurement mode. As a result, the output of laser diode 16a is set to, for example, 10 mW.

In step S109, controller 11 starts counting the time elapsed. If YES in step

S110 after the elapse of a predetermined period of time, controller 11 outputs an ON signal to high-frequency conversion circuit 14 in step S111. Setting unit 11a sets output voltage Vin at timing T1, which is illustrated in FIG. 5A. Controller 11 then outputs an ON signal to high-frequency conversion circuit 14 at timing T2. As a result, laser diode 16a is set to the multi-mode oscillation state, as illustrated in FIG. 5D.

In step S112, controller 11 performs a measurement by causing the measurement specimen to flow through flow cell 110, and stores the measurement data obtained from the measurement in storage unit 18. When the measurement ends, the measurement data stored in storage unit 18 is sent from sample measuring apparatus 10 to analyzer 20 through communication units 19 and 25. Controller 21 of analyzer 20 stores the received measurement data in storage unit 22. In step S113, controller 21 performs an analysis based on the measurement data in accordance with the measurement mode and displays the analysis result on output unit 23 when the analysis ends. Consequently, for example a scattergram illustrated in FIG. 9A, 9B, or 9C or blood-cell counts are displayed on output unit 23.

According to embodiment 1, even when setting unit 11a changes output voltage Vin in accordance with the measurement mode, drive circuit 13 adjusts the current value of the drive signal in accordance with changed output voltage Vin such that the output of laser diode 16a can be constant. In this way, a measurement specimen prepared for a given measurement mode can be stably irradiated with laser light of an intensity suitable therefor.

Regardless of output voltage Vin, high-frequency conversion circuit 14 guides the drive signal outputted from drive circuit 13 to second signal path 103, which is different from first signal path 102, connected to laser diode 16a. In this way, even when the current value of the drive signal outputted from drive circuit 13 is changed, the drive signal to be supplied to laser diode 16a can be converted into a high-frequency signal without performing control that may involve adjusting the high-frequency component such that the high-frequency component is adapted to the change of the drive signal, and superimposing that high-frequency component onto the drive signal. Hence, even when the drive signal is changed, laser diode 16a can easily be set to a multi-mode oscillation state without complicated control.

Also, since five logic circuits 331 to 335 are connected in parallel and connected to output part 14b, the capacitance for guiding the drive signal to the ground is large when the pulse train signal at output part 14b is at the low level. Thus, the drive signal outputted from drive circuit 13 can be efficiently guided to the ground when the pulse train signal at output part 14b is at the low level. Moreover, with five logic circuits 331 to 335 connected in parallel as mentioned above, the amount of current can be large when the pulse train signal at output part 14b is at the high level. Thus, the drive signal outputted from drive circuit 13 can be efficiently prevented from flowing into high-frequency conversion circuit 14.

The number of logic circuits 331 to 335 is not limited to five but may be a different number.

Also, logic circuits 331 to 335 may be logic circuits other than NOT circuits such as AND circuits or OR circuits. In the case where logic circuits 331 to 335 are AND circuits, a high-level voltage is applied to one of the input terminals of each of logic circuits 331 to 335. On the other hand, in the case where logic circuits 331 to 335 are OR circuits, a low level is applied to one of the input terminals of each of logic circuits 331 to 335. In this way, when a high level is applied to the other input terminals of logic circuits 331 to 335, the outputs of logic circuits 331 to 335 shift from a low level to a high level. In the case where AND circuits or OR circuits are used as logic circuits 331 to 335 as above, logic circuit 320 at the previous stage is omitted.

Instead of ring oscillator circuit 310, a different oscillation circuit may be used.

The circuitry of sample measuring apparatus 10 is configured such that the duty cycle of the pulse train signal illustrated in FIG. 5C is 50%, but may be configured such that the duty cycle of the pulse train signal is a value other than 50%. For example, in a case where the duty cycle of the pulse train signal is reduced to 33%, the periods in which the drive signal flows into laser diode 16a is short, thereby making it harder for laser diode 16a to stay in a steady state from a transient response state. In this way, it is easier to maintain laser diode 16a in a multi-mode oscillation state.

However, in the case where the duty cycle of the pulse train signal is reduced to 33% as above, the peaks of the current value of the drive signal flowing into laser diode 16a at and after timing T2 rise to be approximately three times greater than the value from timing T1 to timing T2. Such a rise in the peaks of the current value of the drive signal increases the power consumption for the APC control. Thus, in view of reducing the power consumption, the duty cycle of the pulse train signal is desirably large. For this reason, the duty cycle of the pulse train signal is desirably set by taking into consideration the maintenance of a multi-mode oscillation state and the reduction of the power consumption by drive circuit 13.

Logic circuits 331 to 335 of high-frequency conversion circuit 14 do not necessarily have to be connected to the ground as long as the drive signal outputted from drive circuit 13 is guided to high-frequency conversion circuit 14 during the periods illustrated in FIG. 5C in which the pulse train signal is at the low level.

Embodiment 2

Embodiment 2 is changed from embodiment 1 in the configuration of high-frequency conversion circuit 14. Due to this change, diode 15 is omitted in embodiment 2. The other features of the configuration are similar to embodiment 1.

Figure 10:
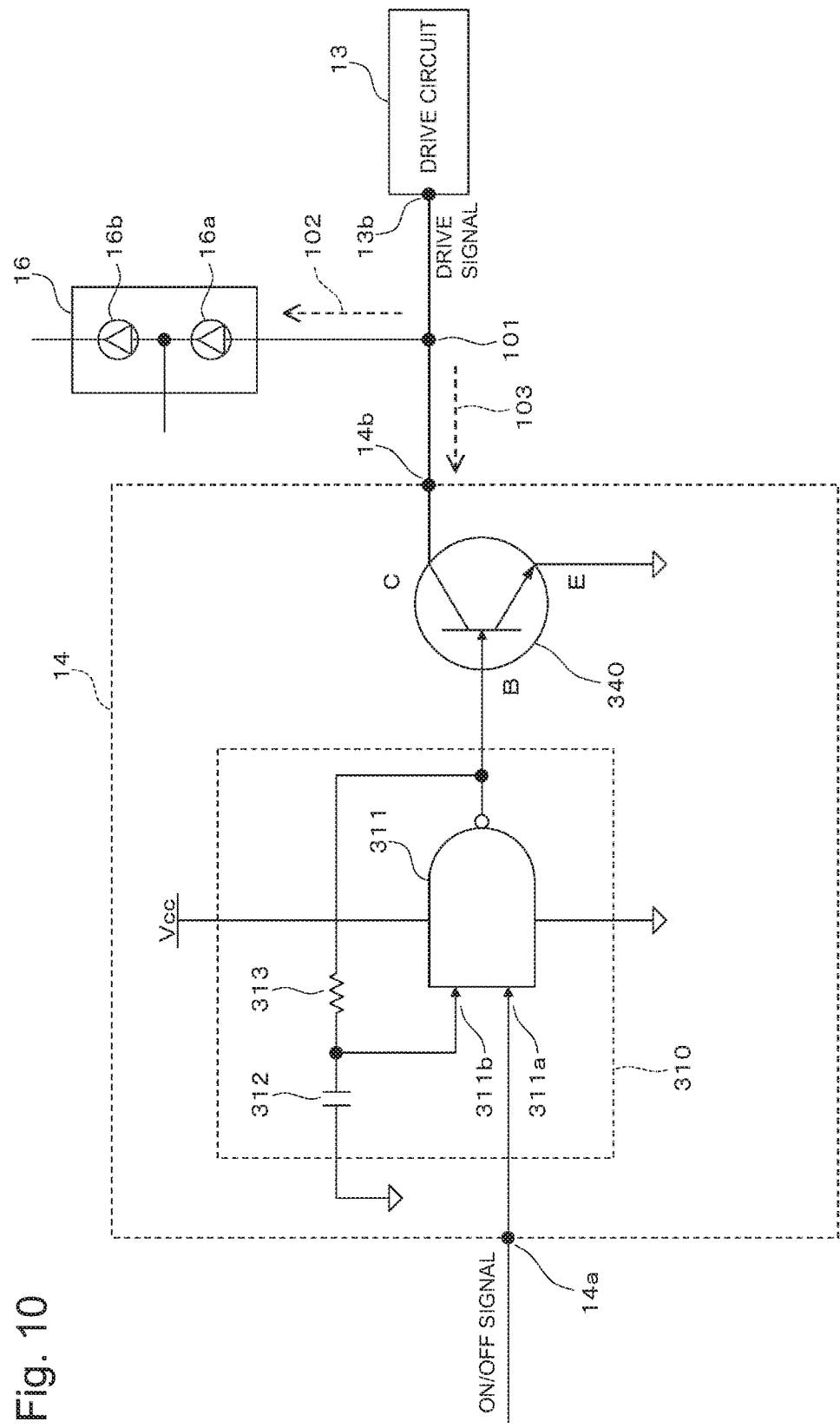
FIG. 10 is a diagram illustrating a circuit configuration of a sample measuring apparatus according to one or more embodiments.

As illustrated in FIG. 10, high-frequency conversion circuit 14 includes transistor 340 instead of logic circuits 320 and 331 to 335. The output signal of ring oscillator circuit 310 is inputted into the base terminal of transistor 340. The emitter terminal of transistor 340 is connected to the ground. The collector terminal of transistor 340 is connected to output part 14b of high-frequency conversion circuit 14.

In this configuration, transistor 340 serves as a switching circuit that guides the drive signal to the ground. When the output signal from ring oscillator circuit 310 is at the low level, current does not flow from the collector terminal to the emitter terminal of transistor 340. Thus, the drive signal outputted from drive circuit 13 does not flow into high-frequency conversion circuit 14 but flows into laser diode 16a.

On the other hand, when the output signal from ring oscillator circuit 310 is at the high level, current flows from the collector terminal to the emitter terminal of transistor 340. Thus, the drive signal outputted from drive circuit 13 does not flow into laser diode 16a but is received by transistor 340 and guided to the ground. In other words, high-frequency conversion circuit 14 guides the drive signal outputted from drive circuit 13 to second signal path 103, which is different from first signal path 102, connected to laser diode 16a, in the predetermined cycle, thereby converting the drive signal to be supplied to laser diode 16a into a high-frequency signal. Thus, the drive signal can be alternately switched between a state of flowing into laser diode 16a and a state of not flowing into laser diode 16a.

Note that, when the output signal from ring oscillator circuit 310 is at the low level, transistor 340 is in a de-actuated state, and the same high-level potential as the potential at output part 13b of drive circuit 13 is generated at output part 14b. On the other hand, when the output signal from ring oscillator circuit 310 is at the high level, transistor 340 is in an actuated state, and the same low-level potential as the ground is generated at output part 14b. Thus, at output part 14b, which is connected to second signal path 103, high-frequency conversion circuit 14 generates a potential switching between the high level and the low level in the predetermined cycle.

In the configuration of embodiment 2, logic circuits 320 and 331 to 335 in FIG. 4 are replaced with single transistor 340, and diode 15 in FIG. 4 is omitted. Hence, the circuit configuration is simplified. Moreover, transistor 340 serves as a switching circuit. Thus, even if drive circuit 13 is actuated to make the potential at output part 13b higher than the potential at output part 14b of high-frequency conversion circuit 14, the drive signal outputted from drive circuit 13 can be guided to laser diode 16a during the periods in which the pulse train signal is at the high level, as in embodiment 1.

In above embodiments 1 and 2, the output of laser diode 16a may be set to be constant irrespective of the measurement mode. In this case, the electric signals outputted from optical detectors 121 to 123 are amplified by a gain suitable for the measurement mode. However, such amplification of the electric signals also amplifies noise components in a similar manner. For this reason, in the case of the configuration in which the output of laser diode 16a is set to be constant irrespective of the measurement mode, the output of laser diode 16a is desirably set to be high in advance. Doing so can make large the differences between the electric signals acquired from the particles and the noises and reduce the influence of the noises on the electric signals. In this configuration, the output of laser diode 16a is set to, for example, about 45 mW.

Note that controller 11, controller 12, and the like in sample analyzer 30 are implemented such that, for example, a circuitry such as one or more central processing units (CPUs) or processors provided in sample analyzer 30 executes a predetermined program(s).

While various embodiments of the present invention have been described above, it should be understood that they have been presented by way of example only and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

The invention claimed is:

1. A sample measuring apparatus comprising:
a laser diode configured to apply laser light to a measurement specimen prepared from a sample;
a detection unit that acquires optical information from a particle in the measurement specimen to which the laser light is applied;
a drive circuit that supplies a direct-current drive signal to the laser diode; and
a high-frequency conversion circuit that generates a potential that switches between a high level and a low level in a predetermined cycle to guide, in the predetermined cycle, the drive signal outputted from the drive circuit to a second signal path which is different from a first signal path connected to the laser diode, thereby converting the drive signal to be supplied to the laser diode into a high-frequency signal.

2. The sample measuring apparatus according to claim 1, wherein the high-frequency conversion circuit outputs a pulse train signal with the potential cycling the high level and the low level in the predetermined cycle, from an output part connected to the second signal path.

3. The sample measuring apparatus according to claim 2, wherein the high-frequency conversion circuit includes a ring oscillator circuit.

4. The sample measuring apparatus according to claim 2, wherein the high-frequency conversion circuit guides the drive signal outputted from the drive circuit to a ground through the second signal path during a period in which the pulse train signal is at the low level.

5. The sample measuring apparatus according to claim 2, wherein the high-frequency conversion circuit includes multi-stage logic circuits that guide the drive signal outputted from the drive circuit to a ground during a period in which the pulse train signal is at the low level.

6. The sample measuring apparatus according to claim 2, wherein a frequency of the pulse train signal is equal to or more than 85 MHz.

7. The sample measuring apparatus according to claim 2, wherein
a signal line connecting the drive circuit and the laser diode is connected to the output part of the high-frequency conversion circuit, and
the high-frequency conversion circuit sets a potential at the output part greater than a potential at the drive circuit during a predetermined period in a single cycle.

8. The sample measuring apparatus according to claim 7, further comprising a diode that is provided between the output part of the high-frequency conversion circuit and the signal line and that causes current to flow in a direction toward the output part.

9. The sample measuring apparatus according to claim 1, further comprising a photodiode that outputs a monitor signal proportional to output of the laser diode, wherein the drive circuit adjusts the drive signal on the basis of the monitor signal such that the output of the laser diode becomes a set value.

10. The sample measuring apparatus according to claim 9, further comprising a setting unit that switches the set value.

11. The sample measuring apparatus according to claim 10, wherein the setting unit changes the set value in accordance with a measurement mode for the sample.

12. The sample measuring apparatus according to claim 11, wherein the high-frequency conversion circuit maintains the high-level potential at a single value greater than a potential at the drive circuit that changes in accordance with the measurement mode for the sample.

13. The sample measuring apparatus according to claim 1, further comprising:
a flow cell through which the measurement specimen is caused to flow;
a light-application optical system that applies the laser light emitted from the laser diode to the measurement specimen flowing through the flow cell; and
a light-reception optical system that guides light generated from the measurement specimen to the detection unit.

14. The sample measuring apparatus according to claim 1, wherein the sample is any one of blood, urine, and epithelium.

15. A sample measuring method comprising:
supplying a direct-current drive signal to a laser diode;
generating a potential that switches between a high level and a low level in a predetermined cycle to guide, in the predetermined cycle, the drive signal to a second signal path which is different from a first signal path connected to the laser diode, thereby converting the drive signal to be supplied to the laser diode into a high-frequency signal;
causing, based on the high-frequency signal, the laser diode to apply laser light to a measurement specimen prepared from a sample; and
acquiring optical information from a particle in the measurement specimen to which the laser light is applied.

16. The sample measuring method according to claim 15, wherein the step of converting the drive signal into the high-frequency signal comprises outputting a pulse train signal with the potential cycling the high level and the low level in the predetermined cycle to the second signal path.

17. The sample measuring method according to claim 16, wherein in the step of converting the drive signal into the high-frequency signal, guiding the drive signal to a ground through the second signal path during a period in which the pulse train signal is at the low level.

18. The sample measuring method according to claim 16, wherein a frequency of the pulse train signal is equal to or more than 85 MHz.

19. The sample measuring method according to claim 15, wherein the sample is any one of blood, urine, and epithelium.

20. The sample measuring method according to claim 15, wherein the optical information is acquired by flow cytometry.

* * * * *